United States Patent [19]

Petersen et al.

[11] 3,981,936

[45] Sept. 21, 1976

[54] METHOD FOR THE PREPARATION OF BIS-(BROMOMETHYL)-TETRACHLOROBENZENES AND THEIR USE AS FLAME-PROOFING AGENTS

[75] Inventors: Egon Petersen, Neunkirchen-Seelscheid; Werner Schmidt, St. Augustin; Klaus-Dieter Steffen, Troisdorf-Oberlar, all of Germany

[73] Assignee: Dynamit Nobel Aktiengesellschaft, Troisdorf, Germany

[22] Filed: Mar. 27, 1974

[21] Appl. No.: 455,153

[30] Foreign Application Priority Data

Mar. 31, 1973 Germany............................ 2316204

[52] U.S. Cl. .................... 200/651 R; 260/45.75 R; 260/45.7 RT
[51] Int. Cl.² .......................................... C07C 25/14
[58] Field of Search ............................... 260/651 R

[56] References Cited
UNITED STATES PATENTS

| | | |
|---|---|---|
| 2,097,155 | 10/1937 | Groll et al. .................... 260/651 R |
| 2,675,413 | 4/1954 | Ballard et al. .................... 260/651 R |
| 3,130,222 | 4/1964 | Asadorian et al. ............... 260/651 R |
| 3,419,626 | 12/1968 | Pyne et al. ...................... 260/651 R |
| 3,420,900 | 1/1969 | Mark.............................. 200/651 R |

*Primary Examiner*—D. Horwitz
*Attorney, Agent, or Firm*—Burgess, Dinklage & Sprung

[57] ABSTRACT

A process for preparing a bis-(bromomethyl)-tetrachlorobenzene which comprises contacting a bis-(chloromethyl)-tetrachlorobenzene with a bromide of an element of the first to the third group of the Periodic Table, preferably in a solvent of the bis-(chloromethyl)-tetrachlorobenzene which solvent is a non-solvent for the bis-(bromomethyl)-tetrachlorobenzene being prepared; a stabilized polymeric composition comprising a polymer and a bis-(bromomethyl)-tetrachlorobenzene, preferably containing additionally a compound of antimony or boron.

11 Claims, No Drawings

METHOD FOR THE PREPARATION OF BIS-(BROMOMETHYL)-TETRACHLOROBENZENES AND THEIR USE AS FLAME-PROOFING AGENTS

BACKGROUND OF THE INVENTION

Field of the Invention

This invention is directed to a method for the preparation of 1,2-, 1,3- or 1,4-bis-(bromomethyl)-tetrachlorobenzenes by reaction of a bis-(chloromethyl)-tetrachlorobenzene with a bromide of an element of group 1 to group 3 inclusive of the Periodic System including HBr. This invention is also directed to the use of a bis-(bromomethyl)-tetrachlorobenzene as a flame retarding agent in synthetic polymer compositions, especially polymer compositions of polycondensation polymers, polyaddition polymers and polymers prepared from polymerization of an unsaturated aliphatic monomer.

DISCUSSION OF THE PRIOR ART

It is known to synthesize 1,2-, 1,3- and 1,4-bis-(bromomethyl)-tetrachlorobenzene from the corresponding tetrachloroxylenes by reaction of bromine in a carbon tetrachloride solution in the presence of a source of radiation supplying ultraviolet light. A reference is made to U.S. Pat. No. 2,564,214; U.S. Pat. No. 2,600,691; U.S. Pat. No. 2,631,168; U.S. Pat. No. 2,702,825; U.S. Pat. No. 3,419,626 and an article in the Journal of Organic Chemistry, vol. 25, page 2106 (1960).

Tetrachloro-o-xylylene dibromide has also been made from tetrachloro-o-xylene and N-bromosuccinimide as reported by W. E. Rosen, V. P. Toohey and A. C. Shabic in the Journal of the Americal Chemical Society, vol. 80 (1958), page 935. This compound has also been prepared from 1,2-bis-(hydroxymethyl)-3,4,5,6-tetrachlorobenzene and hydrogen bromide. See E. L. Schumann, M. G. van Campen and C. H. Tilford, Journal of Organic Chemistry, vol. 23 (1958), page 763.

It has become desirable, however, to provide an inexpensive method for the preparation of bis-(bromomethyl)-tetrachlorobenzenes from reagents which can be readily handled and do not require the additional use of irradiation to supply ultraviolet light. Moreover, it has become desirable to provide a process for the preparation of such bis-(bromomethyl)-tetrachlorobenzenes from agents which are readily available whereby the resultant bis-(bromomethyl)-tetrachlorobenzene is prepared in virtually a stoichiometric amount and in excellent purity.

As indicated above, it has also become desirable to provide a flame-proofing agent for polycondensation and polyaddition products as well as for polymerization products of unsaturated aliphatic monomers or, in the case of copolymers, of at least one aliphatic monomer such as, for example, polyamides like those of aminocarboxylic acids, e.g., epsilonaminocaprylic acid or aromatic or aliphatic dicarboxylic acid such as adipic acid or sebacic acid and long-chained, including branched, diamines such as hexamethylene diamine and its homologs; polyethers such as polyoxymethylene, polyurethane such as polycarboxylic acid esters of diols such as 4,4-dihydroxydiphenyl propane, phenol resins, melamine resins such as reaction products of phenol, kresols or melamine with formaldehyde; epoxy resins such as, for example, diglycidyl ethers of diphenylol propane and its molding materials hardened with hardening agents such as amines or carboxylic acid anhydrides; or saturated or unsaturated polyesters such as reaction products of diols with dicarboxylic acids or lactones, in particular, polyethylene terephthalate, polybutylene terephthalate; polyolefins such as polyethylene, polypropylene, polybutylene, polybutadiene; polyacrylates such as polymethacrylate, polyethylmethacrylate, their copolymers and graft polymers such as those of acrylonitrile or methacrylic acid esters with butadiene and styrene; polyvinyl acetate, polyvinyl alcohol, polyvinyl fluoride and insofar as necessary, polyvinyl chloride and/or vinyl chloride copolymers and others. It is particularly desirable to provide an agent which can be employed as a flame-proofing agent in emulsions and latexes such as SBR latexes.

SUMMARY OF THE INVENTION

The objects of the invention are provided by a process for preparing a bis-(bromomethyl)-tetrachlorobenzene which comprises contacting a bis-(chloromethyl)-tetrachlorobenzene with a bromide of an element of the first to the third group inclusive of the Periodic System or hydrogen bromide. In accordance with the present invention the reaction of a bromide such as sodium bromide with bis-(chloromethyl)-tetrachlorobenzene is preferably carried out employing a stoichiometric amount of bromide relevant to the bis-(chloromethyl)tetrachlorobenzene. Preferably, the reaction is carried out in a solvent of the bis-(chloromethyl)-tetrachlorobenzene which solvent is one in which the bis-(bromomethyl)-tetrachlorobenzene being prepared is substantially insoluble, i.e., the solvent is substantially a non-solvent of the bis-(bromomethyl)-tetrachlorobenzene.

Generally speaking, the bromides which are useful in the chlorine-bromine interchange reaction of the present invention are all those bromides of the elements of groups 1, 2 and 3 of the Periodic System or hydrogen bromide. Thus, there is contemplated the bromides of the following elements: lithium, sodium, potassium, copper, rubidium, cesium, beryllium, magnesium, calcium, zinc, strontium, cadmium, barium, boron, aluminum, preferred those of the first to third main group. Obviously, it is preferred to use those bromides which are readily available and these include, in particular, sodium bromide, potassium bromide, lithium bromide, magnesium bromide, hydrogen bromide and aluminum bromide.

The halogen exchange is carried out in a solvent in which the tetrachloroxylylene dichloride is readily soluble at room temperature or upon heating such as mild heating. This solvent should be one in which the tetrachloroxylylene dibromide is substantially insoluble. Such solvents are alcohols such as methanol, ethanol, propanol, ethers such as tetrahydrofuran or dioxanes, preferred the ketones such as acetone, methylethyl ketone or the pentanons. Of the ketones it is preferred to use acetone. The solvents do not have to be anhydrous and water can be present provided there is no marked degree of hydrolysis of the bromides. In fact the bromide can be introduced in the form of an aqueous solution into a reaction vessel containing the tetrachloroxylylene dichloride.

Generally speaking, the bromide is employed in a stoichiometric amount relevant to the amount of tetrachloroxylylene dichloride. However, an excess of bromide can be employed, especially an excess between 1 and 10%.

The process is generally carried out by contacting the reactants in the solvent at a temperature between 20° and 180°C, preferably between 40° and 150°C. It is particularly advantageous to carry out the reaction at about the boiling temperature of the solvent employed, especially at the boiling temperature of an organic solvent. The bis-(bromomethyl)-tetrachlorobenzene is precipitated already during the reaction and the process is completed by cooling the solution.

The reaction is conducted for a period of time until the desired amount of bis-(bromomethyl)-tetrachlorobenzene is precipitated. Generally speaking, the reaction mixture is stirred for a period of between 1 and 5 hours after all of the reactants are present in the reaction mixture. Preferably, the reaction mixture is stirred for a period of 3 to 4 hours. The reaction is generally conducted by initially dissolving the bromide in a suitable solvent such as acetone or methanol and preferably, to the extent that there are no side reactions such as hydrolysis, they are dissolved in water and added drop by drop in such solution to a solution of tetrachloroxylylene dichloride. The bromide can also be given to the dissolved bis-(chloromethyl)-tetrachlorobenzene in an undissolved crystalline state. Thereafter, the reaction continues with stirring as indicated.

The preparation of bis-(bromomethyl)-tetrachlorobenzene proceeds remarkably well and yields of more than 90% of theory are obtained. The products are obtained also in good purity. The smooth reaction is considered remarkable in view of the general teachings in the art which suggests that such a chlorine-bromine exchange, which represents an equilibrium reaction, usually takes place not completely in spite of an excess of bromide and rather expensive bromides as lithium bromide or aluminum bromide, had to have been used. See Houben-Weyl, Georg Thieme Verlag, Stuttgart (1960) 5/4, page 354.

The bis-(bromomethyl)-tetrachlorobenzenes prepared in accordance with the present process exhibit adequate thermal stabilities for their use as flame-proofing agents. They withstand processing conditions of 120° to 250°C without any difficulties. Hence, they can be readily mixed with or blended with a polymer during the preparation of the polymer. However, they are usually added prior to the time the polymer is formed into a molding composition or into a finished article. For instance, it is generally the practice to add the bis-(bromomethyl)-tetrachlorobenzene to the polymer mass and to form the same into a molding composition.

These bis-(bromomethyl)-tetrachlorobenzenes can be used alone or in combination with other flame-inhibiting additives that, in a given case, may have a synergistic effect. It is particularly contemplated to use these bis-(bromomethyl)-tetrachlorobenzene with antimony compounds, boron compounds and phosphorous compounds. Particularly contemplated are antimony compounds such as antimony trioxide, alkaline earth borate and phosphates. Other suitable antimony compounds are antimony sulfide, sodium antimonite and potassium antimonate. Of the antimony compounds there can also be employed antimony compounds of organic acids, such as, for example antimony butyrates, antimony valerianate, antimony capronate and the like and their pentavalent dihalogen derivatives. The usual additives to the plastic material such as filler, pigments, plasticizers, lubricants and light stabilizers can, of course, also be employed in the fire retardant polymeric composition.

The presence of bromine in addition to chlorine in the bis-(bromomethyl)-tetrachlorobenzene molecules has a particular advantage. It has been surprisingly found that a very good flame inhibiting effect is provided by the use of this comparatively small amount of bromine in relation to the amount of chlorine which is less effective in other cases. The tetrachloroxylylene dibromides are added in quantities of 1 to 30, preferably 5 to 25% by weight based on the polymer and can contain antimony compounds, such as $Sb_2O_3$ in quantities of 0.5 to 15%, preferably 2 to 12%, to achieve an optimum flame inhibiting effect.

DESCRIPTION OF SPECIFIC EMBODIMENTS

There has been set forth above in the paragraphs preceding the summary of this invention a listing of polymers to which the tetrachloroxylylene dibromides can be added. It should be understood that the tetrachlorxylelene can be added to all of these polymers and the manner of the addition is substantially the same from polymer to polymer. Essentially, the dibromide can be added to the mass by milling it together with the polycondensation, polyaddition or unsaturated aliphatic polymer composition whether it be in the form of a homopolymer or copolymer. If milling of the dibromide and polymer presents difficulties, the dibromide composition is introduced into a reaction vessel employed for the preparation of the polymer to be flame inhibited. The resultant composition is one which already contains the flame inhibiting agent.

The self-extinguishing action of the tetrachloroxyledene dibromides in plastics has been rated by means of the "oxygen index" test in accordance with ASTMD 2863-70. This test indicates that the portion of oxygen in an oxygen/nitrogen mixture at which a substance continues to burn independently under defined conditions. Values of between 3 and 4 units above the value for a polymer free of flame-proofing agent represent good results. Naturally, the higher that this value is the better is the flame-proofing effect provided.

The tetrachloroxylelene dibromides have also been evaluated to determine their flame-proofing effect. They were evaluated by a recently developed test of our own, which utilizes suspended plastic rods of the polymeric composition whose flame-proofing characteristics are to be improved. Grades of tests permits the burning characteristics of the suspended plastic rod to be rated. Grades from 1 (very good) to 5 (poor) are assigned depending on the flame exposure time, the after-burn time, the dripping characteristics and the flame propagation and temperature as well as the gas development.

In order to more fully illustrate the nature of the invention and the manner of practicing the same, the following examples are presented. In these examples there are set forth three separate preparations for bis-(bromomethyl)-tetrachlorobenzenes. In each instance a different position isomer of the bis-(bromomethyl)-tetrachlorobenzene was prepared. The examples also compare the effect of the three possible position isomers for the flame-proofing of various polymers. It is seen from these examples that the flame-proofing characteristics is markedly improved by the use of a bis-(bromomethyl)-tetrachlorobenzene. While the addition of another flame-proofing agent other than the bromine containing compound of the present invention improves the flame-proofing characteristics of a polymeric material, the best improvement is obtained by use of the bis-(bromomethyl)-tetrachlorobenzene which acts synergistically to provide superior flame-proof characteristics for the polymeric materials so treated.

EXAMPLE 1

1,4- bis-(bromomethyl-2,3,5,6-tetrachlorobenzene (or tetrachloro-p-xylylene dibromide).

15.64 g. of 1,4-bis-(chloromethyl)-2,3,5,6-tetrachloroxylene (0.05 moles) was dissolved in hot state in 230 ml. of acetone and a solution of 11.3 g. of NaBr (0.11 moles) in approx. 20 ml. water was added thereto drop by drop while stirring. The mixture was heated for 3.5 hours to the boiling point, was cooled, the deposited precipitate was filtered off, washed with water and dried.

Yield: 18.5 g (92.0% of theory). Solidification point: 207°–211°C.

The solidification point was increased to 213° to 215°C by recrystallization from acetone.

EXAMPLE 2

1,3-bis-(bromomethyl)-2,4,5,6-tetrachlorobenzene.

31.3 g of 1,3-bis-(chloromethyl)-2,4,5,6-tetrachlorobenzene (0.1 mole) were dissolved in the hot state in 250 ml. of acetone and a solution of 22.6 g of NaBr (0.22 moles) in approx. 40 ml. of water was added thereto drop by drop. The mixture was heated for 3.5 hours to the boiling point, cooled, washed with water and dried.

Yield: 36.5 g (90.6% of theory). Solidification point: 158°–160°C

The solidification point was raised to 162°–163°C by recrystallization from acetone.

When the reaction was carried out analogously thereto, but a solution of the starting substance in ethanol or tetrahydrofuran was used, corresponding results were obtained upon adding 19.1 g of LiBr or 19.5 g of AlBr$_3$ (dissolved in methanol or ethanol).

EXAMPLE 3

1,2-bis-(bromomethyl)-3,4,5,6-tetrachlorobenzene.

In accordance with Example 2, the o-isomer was produced as well by reaction of 1,2-bis-(chloromethyl)-3,4,5,6-tetrachlorobenzene with NaBr added in water into an acetone solution of 1,2-bis-(chloromethyl)-3,4,5,6-tetrachlorobenzene in acetone.

Yield: 35.8 (89.1% of theory). Solidification point: 112°–115°C.

The solidification point was raised to 116°–118°C by recrystallization from acetone.

EXAMPLE 4

The weight ratios listed in the table below of 1,4-bis-(bromomethyl)-2,3,5,6-tetrachlorobenzene (A), 1,3-bis-(bromomethyl)-2,3,5,6-tetrachlorobenzene (B) or 1,2-bis-(bromomethyl)-3,4,5,6-tetrachlorobenzene (C) were worked at elevated temperature on a rolling system into some plastics listed as well in the table below. Rods were pressed of these materials treated in this manner, and the oxygen index was determined.

| Polymer | Flame-Proofing Agent | | | Oxygen Index | Comparison Values Oxygen Index* |
|---|---|---|---|---|---|
| | Comp. | (% by wt.) | Sb$_2$O$_3$ (% by wt.) | | |
| Polycarbonate | A | 15 | — | 37 | 24 – 25 |
| (Makrolon 3000) | A | 15 | 5 | 42 | |
| | B | 15 | 5 | 42 | |
| | C | 15 | 5 | 42 | |
| Polyethylene | A | 15 | — | 23 | 18 – 19 |
| (Low-Pressure Polyethylene) | A | 15 | 5 | 27 | |
| | B | 15 | 5 | 27 | |
| | C | 15 | 5 | 27 | |
| ABS- | A | 15 | — | 22 | 18 – 20 |
| Graft Polymer | A | 15 | 5 | 25 | |
| | B | 15 | 5 | 24 | |
| | C | 15 | 5 | 24 | |

*for the respective polymer without addition of flame-proofing agents

EXAMPLE 5

In accordance with the test described below, plastics rods of 2 × 20 × 240 mm. were suspended perpendicularly in an appropriate holding device in a square protective box which was open at the top and on one side and was exposed at the lower end to a non-luminous, horizontal bunsen burner flame which was aimed perpendicularly at the lower edge of the specimen at a distance of 10 cm. The behavior of the specimen was observed, and grades from 1 to 5 were assigned depending on the flame exposure time, after-burn time, dripping characteristics and other criteria. The aforementioned grades were defined as follows:

1. The specimen went out immediately after removal of the igniting flame following a flame exposure time of at least 10 seconds; any portions that might drip off did not burn.

2. The specimen went out a few seconds after removal of the source of ignition; portions that dripped off went out while dripping off.

3. The specimen continued to burn after removal of the source of ignition, but went out after a short period of time: dripping portions had a short after-burn period.

4. The specimen continued to burn after removal of the source of ignition and went out as a result of the dripping off of the burning end: dripping portions continued to burn for a relatively long period of time.

5. The specimen burned off completely after removal of the igniting flame, and so did dripping portions.

The grades listed in the table below represent the average value from 10 tests.

| Polymer | Flame-Proofing Agent Bis-(bromomethyl)-tetra-chlorobenzene | $Sb_2O_3$ | Grade | * |
|---|---|---|---|---|
| Polyethylene | A, 15% by wt. | 3% by wt. | 2 | SE II |
|  | A, 20% by wt. | 5% by wt. | 1–2 | SE 0 |
| Polypropylene | A, 15% by wt. | 5% by wt. | 1–2 | SE II |
|  | A, 20% by wt. | 5% by wt. | 1–2 | SE II |
| ABS | A, 15% by wt. | 5% by wt. | 3 | — |
|  | A, 20% by wt. | 5% by wt. | 1–2 | SE II |
| Polypropylene | B, 20% by wt. | 5% by wt. | 1–2 | SE II |
|  | C, 20% by wt. | 5% by wt. | 1–2 | — |
| Polytetramethyl-ene-terephthal-ate | A, 9% by wt. | 5% by wt. | 3 | SE 0 |
|  | B, 9% by wt. | 5% by wt. | 3 | — |
|  | A, 16% by wt. | 5% by wt. | 2 | — |
|  | B, 16% by wt. | 5% by wt. | 2 | — |
| Polystyrene | A, 15% by wt. | — | — | SE II |
|  | B, 20% by wt. | — | — | SE 0 |

For polyethylene and ABS, the same grades were obtained with the flame-proofing agents B (the meta isomer) or C (the ortho isomer) as with agent A (the para isomer).
*Flametest according UL 94 - test method, developed by underwriters laboratories, performed with test specimens of 1/16 inch thickness, containing no additional antimony compound.

EXAMPLE 6

For comparative purpose 1,4-bis-(chloromethyl)-tetrachlorobenzene is tested by the test method of example 5. The found grades are considerably worse, compared with the values of example 5 for the respective polymers.

| Polymer | | | Grade |
|---|---|---|---|
| Polyethylene | 15 % by wt. | 5 % by wt. $S_2O_3$ | 3 |
|  | 20 % by wt. | 5 % by wt. $S_2O_3$ | 2 |
| Polypropylene | 15 % by wt. | 5 % by wt. $S_2O_3$ | 4–3 |
|  | 20 % by wt. | 5 % by wt. $S_2O_3$ | 4–3 |
| ABS | 15 % by wt. | 5 % by wt. $S_2O_3$ | 3 |
|  | 20 % by wt. | 5 % by wt. $S_2O_3$ | 3–2 |

The 1,4-bis-(chloromethyl)-tetrachlorobenzene for this purpose and as raw material for the process can be produced by method of German Pat. No. 1,568,607.

What is claimed is:

1. A process for preparing a bis-(bromomethyl)-tetrachlorobenzene which comprises contacting a bis-(chloromethyl)-tetrachlorobenzene at a temperature between 20° and 180°C with a bromide of an element of group 1 to group 3 inclusive of the periodic system or hydrogen bromide in a solvent for said bis-(chloromethyl)-tetrachlorobenzene in which solvent the corresponding bis-(bromomethyl)-tetrachlorobenzene is substantially insoluble, said solvent being selected from the group consisting of alcohols, ethers and ketones.

2. A process according to claim 1 wherein the bromide is introduced into a reaction vessel containing bis-(chloromethyl)-tetrachlorobenzene in solution in the form of a solution.

3. A process according to claim 1 wherein the solvent is selected from the group consisting of acetone or methanol in the presence of water.

4. A process according to claim 3 wherein the bromide is selected from the group consisting of hydrogen bromide, sodium bromide, potassium bromide, lithium bromide, magnesium bromide and aluminum bromide.

5. A process according to claim 4 wherein the bromide is sodium bromide.

6. A process according to claim 1 wherein the reaction is carried out at a temperature between 40° and 150°C.

7. A process according to claim 1 wherein the reaction is carried out with stirring for a period of 1 to 5 hours.

8. A process according to claim 7 wherein the reaction is carried out with stirring for a period of between 3 and 4 hours.

9. A process according to claim 1 wherein the bis-(chloromethyl)-tetrachlorobenzene is 1,2-bis-(chloromethyl)-tetrachlorobenzene.

10. A process according to claim 1 wherein the bis-(chloromethyl)-tetrachlorobenzene is 1,3-bis-(chloromethyl)-tetrachlorobenzene.

11. A process according to claim 1 wherein the bis-(chloromethyl)-tetrachlorobenzene is 1,4-bis-(chloromethyl)-tetrachlorobenzene.

* * * * *